United States Patent
Annio et al.

(10) Patent No.: US 11,852,704 B2
(45) Date of Patent: Dec. 26, 2023

(54) MOTOR FOR A MR ELASTOGRAPHY TRANSDUCER

(71) Applicants: Siemens Healthcare GmbH, Erlangen (DE); Centre National de la Recherche Scientifique (CNRS), Paris (FR); Institut National de La Sante et de la Recherche Medicale (INSERM), Paris (FR); King's College London, London (GB); Department of Health and Human Services, Bethesda, MD (US); UNIV PARIS XIII PARIS-NORD VILLETANEUSE, Villetaneuse (FR); Universite de Paris, Paris (FR)

(72) Inventors: Giacomo Annio, Mola di Bari Ba (IT); Verena Muller-Reinwald, Bayern (DE); Ralph Sinkus, Parmain (FR); Omar Darwish, London (GB); Wilfried Schnell, Forchheim (DE); Tamara Elisabeth Falkner, Schwabach (DE); Ahmed M. Gharib, Bethesda, MD (US)

(73) Assignees: Siemens Healthcare GmbH, Erlangen (DE); Centre National de la Recherche Scientifique (CNRS), Paris (FR); Institut National de La Sante et de la Recherche Medicale (INSERM), Paris (FR); King's College London, London (GB); Department of Health and Human Services, Bethesda, MD (US); UNIV PARIS XIII PARIS-NORD VILLETANEUSE, Villetaneuse (FR); Universite de Paris, Paris (FR)

(*) Notice: Subject to any disclaimer, the term of this patent is extended or adjusted under 35 U.S.C. 154(b) by 0 days.

(21) Appl. No.: 17/697,492

(22) Filed: Mar. 17, 2022

(65) Prior Publication Data

US 2023/0296708 A1     Sep. 21, 2023

(51) Int. Cl.
*G01R 33/48* (2006.01)
*A61B 5/055* (2006.01)
(Continued)

(52) U.S. Cl.
CPC ............ *G01R 33/48* (2013.01); *A61B 5/055* (2013.01); *G01R 33/56358* (2013.01); *A61B 5/704* (2013.01)

(58) Field of Classification Search
CPC ............................................. G01R 33/56358
See application file for complete search history.

(56) References Cited

U.S. PATENT DOCUMENTS

| 2005/0270029 A1* | 12/2005 | Ehman | A61B 5/055 |
| | | | 324/318 |
| 2009/0143679 A1* | 6/2009 | Salcudean | A61B 8/12 |
| | | | 600/443 |

(Continued)

FOREIGN PATENT DOCUMENTS

WO     2016135493 A2     9/2016

OTHER PUBLICATIONS

Runge J. et al.:"A novel magnetic resonance elastography transducer concept based on a rotational eccentric mass: preliminary experiences with the gravitational transducer" Physics in Medicine & Biology, 64(4), 045007, 2019.
(Continued)

*Primary Examiner* — G. M. A Hyder
(74) *Attorney, Agent, or Firm* — Banner & Witcoff, Ltd.

(57) ABSTRACT

The present disclosure is directed to a motor for a magnetic resonance (MR) tomography room, to a patient table for the
(Continued)

Figure 1:
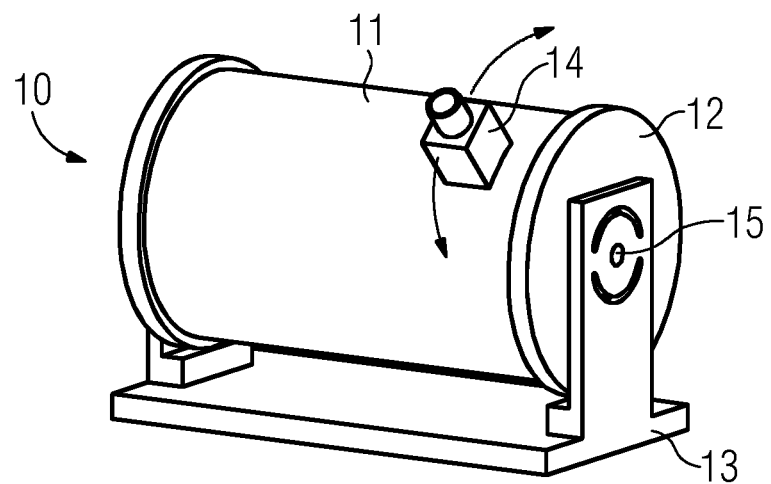

MR room, to a MR elastography device, and to a MR tomography device. A MR tomography device for a MR elastography imaging protocol is arranged within the MR tomography room, and includes a rotational drive for supplying rotational energy to power a MR elastography transducer usable during the MR elastography imaging protocol, and a support structure. The rotational drive comprises a terminal for connecting the MR elastography transducer to the rotational drive, and a bearing means configured such that the position of the terminal relative to the support structure is adaptable along a trajectory predetermined by the bearing means. The rotational drive is mounted to the support structure via the bearing means.

18 Claims, 3 Drawing Sheets

(51) Int. Cl.
*G01R 33/563* (2006.01)
*A61B 5/00* (2006.01)

(56) References Cited

U.S. PATENT DOCUMENTS

| | | | |
|---|---|---|---|
| 2009/0299168 A1* | 12/2009 | Ehman | A61B 8/485 600/410 |
| 2010/0130856 A1* | 5/2010 | Sack | A61B 8/485 600/438 |
| 2011/0006767 A1* | 1/2011 | Sack | A61B 5/0051 324/309 |
| 2016/0334484 A1 | 11/2016 | Wirtz et al. | |
| 2018/0172789 A1* | 6/2018 | Sinkus | G01R 33/56308 |
| 2018/0292501 A1* | 10/2018 | Neumann | B06B 1/186 |

OTHER PUBLICATIONS

Tse, Z T H et al: "Magnetic Resonance Elastography Hardware Design: A Survey", Proceedings of The Institution of Mechanical Engineers Journal of Engineering in Medicine, Part H, Mechanical Engineering Publications Ltd, London, GB; vol. 223; No. 4; May 1, 2009 (May 1, 2009); pp. 497-514; XP009163292; ISSN: 0954-4119; DOI. 10.1243/09544119JEIM529.

* cited by examiner though in a high (by physical) energy level compared to their physical surrounding. By applying magnetic field gradients in combination with a radio frequency signal, the spins can be excited and emit, during their relaxation into a lower energy level, an electromagnetic MR signal. Based on these MR signals an MR image and/or MR spectroscopic data is calculated.

MOTOR FOR A MR ELASTOGRAPHY TRANSDUCER

TECHNICAL FIELD

The invention relates in one aspect to a motor for a magnetic resonance (MR) tomography room, in another aspect to a patient table for the MR room, in another further aspect to a MR elastography device and in a further aspect to a MR tomography device.

BACKGROUND

In the following, where appropriate throughout the application, the characteristic prefix "magnetic resonance" is abbreviated by "MR". MR elastography is a non-invasive imaging technique. It is in particular used for a quantitative assessment of a viscoelastic parameter of tissue of a patient. Therefore, a propagation of mechanical shear waves is imaged using a MR tomography device. The mechanical shear waves are induced by mechanical vibrations. Runge et al. describe in "A novel MR elastography transducer concept based on a rotational eccentric mass: preliminary experiences with the gravitational transducer", Phys. Med. Biol. 64, 2019, 045007 (12 pp), https://doi.org/10.1088/1361-6560/aaf9f8, a MR elastography transducer to generate such mechanical shear waves in the tissue. For example, the mechanical vibrations are generated by rotating an eccentric mass within said MR elastography transducer. Such a transducer is also called gravitation transducer. The rotation of an eccentric mass is similarly known from vibrating alert motors in mobile phones or in compaction plate motors.

WO 2016/135 493 A2 discloses embodiments with a magnetic resonance (MR) compatible transducer for magnetic resonance elastography applications having a cantilevered drive element a free end of which is arranged in use to move reciprocally, and a flexible non-conductive connection rod slidably disposed within a flexible non-conductive sleeve. The connection rod is affixed at a proximal end to the cantilevered drive element via a proximal flexible connection piece that in use accommodates the slight rotational movement of the cantilevered drive element as it reciprocates about its secured end, whilst translating the rotational reciprocation of the cantilevered drive element into a pure translational reciprocation of the connection rod within the sleeve. The distal end of the connection rod is affixed against a protrusion connected to another cantilevered driven element, upon which is mounted a piston element that in use contacts the subject. The distal end of the connection rod is provided with a distal flexible connection piece that forms the connection between the end of the connection rod and the cantilevered driven element, again to account for the pure translational movement of the rod being converted to rotational movement of the cantilevered driven element about its cantilever pivot point.

Another embodiment is known from WO 2016/135 493 A2, which consists of a motor attached to a shaft which transmits the vibration to the front end module to generate a mechanical oscillation at the patient. This motor may be MR compatible and sit within the MR room or alternatively may be MR incompatible and reside in the MR control room. The shaft may be flexible or inflexible and transmits the motion of the motor by rotation.

Depending on the distance between the motor and the MR tomography device the length of the shaft could introduce in the system unwanted frequencies which lead to inaccuracies during the MR elastography imaging. Furthermore, such system could be bulky and/or impede the freedom of movement of a MR tomography device operator and/or a patient. Additionally, such system could be prevented from an integration in the clinical workflow.

SUMMARY

The underlying technical problem of the invention is to provide in one aspect a motor for a MR tomography room, in another aspect a patient table for the MR room, in another further aspect a MR elastography device and in a further aspect a MR tomography device, all of those improved to overcome the aforementioned challenges and to provide better integration and/or more flexibility.

This problem is solved by the features of the independent claims. Advantageous embodiments are disclosed within the dependent claims.

The invention relates in one aspect to a motor for a MR tomography room, wherein a MR tomography device for a MR elastography imaging protocol is arranged within the MR tomography room, comprising:
  a rotational drive for supplying rotational energy to power a MR elastography transducer usable during the MR elastography imaging protocol and
  a support structure,
  wherein the rotational drive comprises a terminal for connecting the MR elastography transducer to the rotational drive,
  characterized in
  a bearing means configured such that the terminal relative to the support structure is movable along a trajectory predetermined by the bearing means,
  wherein the rotational drive is mounted to the support structure via the bearing means.

One advantage of the motor is the additional degree of freedom by having the bearing means. The latter advantageously improves the handling of the motor when used for the MR elastography imaging protocol. Thereby, the motor can be integrated into the clinical workflow much better. The additional degree of freedom allows for compensating the varying position of the MR elastography transducer when connected to the motor via a non-telescopic and/or inelastic shaft.

Another advantage of the suggested motor is that the limiting of unwanted frequencies to be generated achieves more accurate MR elastography imaging. The limitation is made possible by reducing the length of the shaft and thereby the number of rotating shaft sections to one. Alternatively or additionally, the amount of rotational energy can be lowered by the reduced the length.

The MR tomography room is typically characterized by a reduced number of electronic and/or electric devices which could disturb the magnetic fields and/or radio frequency (RF) signals generated within such room. To avoid and/or limit such disturbance, MR compatible materials and/or devices are advantageously used within such room and/or nearby or in the MR tomography device. The MR compatibility can be achieved by choosing specific materials and/or by applying shielding means.

The MR tomography device typically generates a static main magnetic field having a symmetry axis through the bore of the MR tomography device. The main magnetic field is, for example, generated by a main magnet and can comprises a magnetic field strength in the range of 0.5 to 10 T, in particular of 1.5 T, 3 T or 7 T. The main magnetic field, which is also called B0-field, align the spins within the tissue.

During a conventional MR imaging protocol typically a patient is arranged within the main magnetic field in the bore of the MR tomography device and gradient coils are used to spatially encode the spins in the tissue which allows to selectively induce MR signals by sending RF signals. The induced MR signals are received by a MR coil having at least one coil element. The coil element could also be used to send the RF signal for inducing the MR signal in the tissue. Typically, such MR coil is configured for parallel signal acquisition and/or sending.

A specific subset of MR imaging protocols are MR elastography imaging protocols. Such a protocol is typically based on generating mechanical vibrations at a prescribed frequency using an external hardware (such as the motor and the MR elastography transducer) and thereby encoding the wave displacement in the phase of a MR signal of a MR elastography imaging protocol, usually using bipolar gradient waveforms. The mechanical vibrations are advantageously synchronized to the MR elastography imaging protocol and the wave displacement is usually measured at different wave phases.

The motor for the MR tomography room is typically MR compatible such that it does not influence the main magnetic field at all, in particular does not dynamically influence the main magnetic field. The motor is advantageously designed to reside within the MR tomography room without impeding the MR elastography imaging protocol or any other MR imaging protocol. The motor is in particular embodied to reside within a peripheral or central area of the main magnetic field. The motor for the MR tomography room is in particular a motor configured to be arranged within the magnetic field of the MR tomography device, wherein the term "within" includes the area of static as well as increasing and decreasing magnetic field strength. The motor, in particular the rotational drive and/or the support structure, is typically usable during the MR elastography imaging protocol.

The rotational drive for supplying the rotational energy is typically powered by electrical energy provided via an electric plug and/or an electric battery. The rotational drive can typically convert the electrical energy into the rotational energy. The motor can comprise a gear box unit and/or transformer for supporting the rotational drive.

The provided rotational energy is typically sufficient to power the MR elastography transducer. The provided rotational energy is in particular a mechanical energy and not an electrical energy. The powering the MR elastography transducer comprises usually driving the MR elastography transducer such to conduct the MR elastography imaging protocol. Typically, the MR tomography device comprises another power supply to send RF signals and/or receive the MR signals and/or cool the main magnet.

The MR elastography transducer to be powered via the rotational energy is typically a MR compatible transducer such as described by Runge et al. or in WO 2016/135 493 A2. Such transducer could comprise a rotationally mounted eccentric mass arranged to rotate within a transducer container having at least one outer surface that in use transmits vibrations to contacting objects; a driveshaft, functionally connected to the rotationally mounted eccentric mass and arranged to impart rotational energy to the rotationally mounted eccentric mass; wherein the mass, transducer container, and driveshaft are made from MR compatible material. The MR elastography transducer is in particular a gravitational transducer. The MR elastography transducer is typically used during the MR elastography imaging protocol.

The terminal for connecting the MR elastography transducer is in particular embodied to receive the driveshaft of the MR elastography transducer and to couple the driveshaft to the rotational drive. The terminal is in particular a socket. The terminal connects typically the inside of the container with the outside of the container.

The support structure is typically stationary. The support structure is in particular a means to keep the motor stationary and/or relatively static. In other words, the support structure preferably connects the motor with its surrounding, e.g. the floor and/or a patient table. The support structure can comprise a relatively heavy element to hold the motor by earth gravitation and/or friction. Additionally or alternatively, the support structure can comprise a fixing means such as a screw and/or a socket and/or a bolt and/or a stand to engage with the surrounding. The support structure can comprise a damping means to reduce the effect of vibrations on the surrounding due to the rotational energy.

Being mounted to the support structure via the bearing means allows the rotational drive a motion relative to the support structure. The rotational drive is typically movable relative to the support structure such that solely the bearing means predetermines the degree of freedom along the trajectory. The mounting typically comprises a certain kind of fixation.

The bearing means typically comprises at least two parts, the first part being embodied into the support structure, the second part being embodied into the container or vice versa. Basically, it is possible that only the support structure or the container comprise or serve as the bearing means. For example, the mounting point between the container and the support structure could serve as bearing means. The container or the support structure can comprise the mounting point or several mounting points. The mounting point defines usually a point of mechanic interaction between the support structure and the container.

The bearing means advantageously permits at least one of the following motions along the trajectory: a radial rotation, a linear motion, a spherical rotation, a hinge motion. In particular thereby, the bearing means predetermines the trajectory. The trajectory is in particular predetermined when the container is mounted to the support structure via the bearing means. The trajectory allows the motion of the terminal typically along at least one spatial axis. Depending on the kind of the bearing means, it can occur partially along a vertical spatial axis and/or partially along a horizontal spatial axis, for example.

The bearing means is in particular a passive element, typically not driven by the motor. That is, the motion of the terminal relative to the support structure along the trajectory depends on an external force, interacting in particular with the terminal and/or working on the terminal. The motion of the terminal along the trajectory can result from the earth gravitation acting on the terminal.

Additionally or alternatively, the motion of the terminal can result from the driveshaft being connected to the terminal and from a motion of the driveshaft relative to the terminal. Furthermore, if the driveshaft is connected to the terminal, a motion of the MR elastography transducer over a certain distance (larger than the vibrational amplitude) is usually restricted by the driveshaft. The MR elastography transducer can typically be moved by an MR tomography device operator and/or together with the patient table on which the MR elastography transducer is directly or indirectly fixed. It can be indirectly fixed by being fastened to the patient on the patient table or directly to the patient table.

The driveshaft which is further linked to the terminal can push or pull the terminal along the trajectory according to the moving transducer. The pushing or pulling can confer the external force yielding in the motion of the terminal relative to the support structure along the trajectory. Typically, the distance along the transducer is moved correlates with the amount of the trajectory covered during the motion of the terminal. Depending on the kind of bearing means, e.g. if embodied for a linear motion, the distance along the transducer is moved can correspond to the distance the terminal is moved relative to the support structure. Regularly, some of the moved distance of the MR elastography transducer is transformed into deforming the driveshaft, in particular into bending the driveshaft.

One embodiment of the invention relates in one aspect to that the bearing means comprises a rotor bearing, wherein the support structure is the stator and the container is the rotor. The rotor bearing permits in particular a radial rotation. The trajectory comprises therefore typically at least a radial part. This embodiment is in particular advantageous because it allows to compensate a large amount of the moved distance of the MR elastography transducer, in particular by allowing the driveshaft to bend, while the motor comprises a relatively small footprint compared to a bearing means with linear motion. In this embodiment, moving the MR elastography transducer typically confers energy acting on the terminal as rotational energy such that the container as rotor rotates. In this embodiment it can be in particular advantageous, if the support structure is rigidly fixed to the surrounding.

One embodiment of the invention relates in one aspect to that the motor additionally comprises a container, wherein the rotational drive is arranged within the container. The container of the motor is in particular made from MR compatible material. The wall of the container can alternatively be made of a shielding material to shield the rotational drive inside from the main magnetic drive outside. One advantage of this embodiment is that the rotational drive and/or its internal elements are covered by the container. Another advantage is the improved degree of safety and/or durability.

One embodiment of the invention relates in one aspect to that the container is fixed rigidly to the rotational drive such that the trajectory of the terminal substantially corresponds to a trajectory of the container, wherein the terminal is arranged in the lateral wall of the container. The rotational drive is typically arranged within the container such that the position of the rotational drive relative to the wall of the container is fixed. The rotational drive is usually rigidly connected to the wall of the container. The terminal can typically break through the wall of the container. This embodiment is typically advantageous because the closed container protectively shields the inside of the container.

One embodiment as alternative to the previous embodiment relates in one aspect to that the container comprises a slit, wherein the terminal is movably mounted relative to the slit. The rotational drive in particular is movably mounted relative to the slit. The terminal can in particular move within the slit. E.g. if the rotational drive is configured as rotor, the terminal can rotate within the slit. The slit typically connects the inside of the container with the outside of the container. The slit is an opening in the wall of the container. The slit is typically lengthy. The length of the slit is typically less than 360°, typically than 270°, advantageously than 180°, in particular preferably than 90° with reference to the circumference of the container. The slit is typically aligned with the trajectory, e.g. parallel to the trajectory. One advantage of this embodiment is that less moving, in particular rotating parts of the motor are exposed to its surrounding, in particular the user or medical doctor within the MR room. Thereby the degree of safety using such motor is further increased.

One embodiment of the invention relates in one aspect to the container which is cylindric wherein the terminal and/or the slit is arranged in the lateral wall. The cylindric shape is advantageous since the position adaption can be easier due to less outer corners. In particular if the bearing means comprises a rotor bearing, the rotational symmetry of the cylinder can advantageously support the rotation of the container. For the sake of clarity, the overall cylindric shape is in particular interrupted by the terminal and/or the slit. The arrangement of the terminal and/or the slit in the lateral wall typically gives a larger trajectory compared to a position in the top base or bottom base.

One embodiment of the invention relates in one aspect to the motor which comprises an output interface wherein the output interface is configured to provide a rotational frequency signal relative to a rotational frequency and/or phase of the rotational drive. The rotational frequency signal correlates or corresponds to in particular the rotational frequency and/or phase of the rotational drive. The rotational frequency signal can be transmitted via the output interface to a control unit. The output interface can be a wired or wireless interface.

One embodiment of the invention relates in one aspect to the terminal which is configured to provide a locknut connection. In this case typically the driveshaft is similarly or complementarily embodied to such locknut connection.

One embodiment of the invention relates in one aspect to the rotational drive which comprises a stepper motor to generate the rotational energy. Within the container there can be a stepper motor control unit for controlling the stepper motor. The stepper motor advantageously can provide thousands of micro-steps per second, e.g. by using the gear box unit.

The invention relates in one aspect to a patient table for the MR room, comprising:
 a tabletop for bearing a patient,
 a holding means,
 the motor,
 wherein the support structure of the motor is fastened to the patient table via the holding means and
 wherein the tabletop is movable relative to the holding means.

One advantage of the patient table with the connected motor is the increased product integrity allowing freedom of movement for an MR tomography device operator and/or patient. Comprising the motor, the patient table also shares its advantages as described before.

The patient table for the MR room is in particular MR compatible. The patient table, in particular, the tabletop is configured to move a patient within the main magnetic field inside of the bore of the MR tomography device.

The tabletop is usually configured to be moved along the symmetry axis. The tabletop is typically embodied to be moved along a vertical spatial axis and/or a horizontal spatial axis. The movement of the tabletop occurs in particular relative to the holding means and thereby to the connected motor. The movement of the tabletop occurs typically along a straight line.

The holding means of the patient table are in particular configured to interact with the fixing means of the support structure. The holding means can be configured equally or similarly to the fixing means or complementary to the fixing means. By being fastened to the patient table the motor is kept relatively static. It can be possible, that the holding means are configured such that the motor can be disconnected from the holding means.

One embodiment of the invention relates in one aspect to that the holding means and the support structure comprise such a configuration that a longitudinal axis of the tabletop is parallel to at least one spatial axis of the trajectory. The trajectory and the tabletop are advantageously aligned. The longitudinal axis of the tabletop is typically parallel or identical to the symmetry axis of the main magnetic field. This embodiment allows advantageously an automatic orientation, if the driveshaft is connected to the terminal, in a straight position when the patient is in the bore, avoiding parasite frequencies to appear in the system and/or possible rupture of the rotating shaft.

One embodiment of the invention relates in one aspect to that the configuration is embodied such that the trajectory separates the tabletop in two equally sized areas. The configuration is in particular such that the terminal and its trajectory is in the middle of and/or extends centrally over the tabletop. In other words, the configuration allows that the driveshaft, if connected to the terminal, basically is arranged centrally over the tabletop. Alternatively, the configuration can be such that the trajectory can extend aside the tabletop.

One embodiment of the invention relates in one aspect to that the bearing means comprises a rotor bearing, wherein the support structure is the stator and the rotational drive is the rotor, and wherein a rotational axis of the rotational drive is parallel to the floor, on which the patient table is arranged. The rotational axis can be the symmetry axis if the container is cylindric. This embodiment improves in particular the position of the motor and/or of the trajectory. Advantageously, the rotational axis stands perpendicular to the longitudinal axis of the tabletop.

One embodiment of the invention relates in one aspect to that a damping means is provided between the support structure and the patient table to reduce mechanical vibrations. This embodiment may advantageously improve the patient's comfort. The damping means can comprise an elastic material and/or a spring.

The invention relates in one aspect to a MR elastography device, wherein the MR elastography device comprises:
 the motor or
 a patient table having such motor,
 the MR elastography transducer configured to transmit vibration to a patient in dependence of the rotational energy during the MR elastography imaging protocol and
 a driveshaft which is connected to the terminal of the motor to confer the rotational energy from the rotational drive to the MR elastography transducer.

Comprising the motor, the MR elastography device also shares its advantages as described before. Furthermore, the MR elastography comprises a higher usability due to the advantageous varying distance compensation between the terminal and the MR elastography transducer.

The driveshaft connects the terminal with the MR elastography transducer. For this connection, the driveshaft can comprise a single driveshaft section or several interconnected driveshaft sections. In particular, since the motor can be placed nearby to the MR elastography transducer, the driveshaft ideally comprises only the single driveshaft section. The driveshaft is in particular connected to the transducer using a locknut connection. The driveshaft can comprise a rotating core for conferring the rotational energy within a non-rotating sheath.

One embodiment of the invention relates in one aspect to that the driveshaft is configured to bend in a loop depending on the position of the MR elastography transducer relative to the terminal. Typically, the bending of the driveshaft doesn't completely compensate the varying distance between the terminal and the MR elastography transducer. In other words, the motion of the terminal along the trajectory can occur at the same time with the bending of the driveshaft.

One embodiment of the invention relates in one aspect to that the driveshaft is made from a flexible plastic material, such as PEEK. PEEK stands for polyether ether ketone. PEEK is in particular advantageous for being a robust and MR compatible material.

One embodiment of the invention relates in one aspect to that the driveshaft comprises a universal joint. The universal joint can in particular be embodied as Cardan joint. In particular the rotating core of the driveshaft can comprise the universal joint. The universal joint advantageously connects two elements of the rotating core, one connected to the rotational drive, the other connected to the MR elastography transducer. Using such MR elastography device is in particular advantageous because the MR elastography transducer is operative irrespective of the distance between the MR elastography device and the motor.

The invention relates in one aspect to a MR tomography device for a MR elastography imaging protocol, wherein the MR tomography device comprises:
 the main magnet for generating the main magnetic field and
 the MR elastography device.

Comprising the motor, the MR tomography device also shares its advantages as described before. The MR tomography device is in particular embodied to conduct the MR elastography imaging protocol which typically requires the application of such MR elastography device. Due to reduction of the unwanted frequencies, the images reconstructed from the MR elastography imaging protocol can comprises a higher image quality.

One embodiment of the invention relates in one aspect to that the MR tomography device comprises an input interface which is configured to receive a rotational frequency signal relative to a rotational frequency and/or phase of the rotational drive and a control unit configured to control the imaging of the patient according to the MR elastography imaging protocol such that the imaging is performable at least temporarily in synchrony with the rotational frequency signal. The input interface can be embodied to communicate with the output interface of the motor, e.g. by a wired or wireless connection. The control unit can be part of a computing unit. Typically, the MR elastography imaging protocol is personalized for the patient to be imaged. That is, the MR elastography imaging protocol typically varies between different patients, e.g. in terms of the field of view to be imaged. The control unit controls the imaging of the patient such that the MR signals are synchronized to the frequency of the rotational drive at least during the elastography image acquisition. Usually, the MR elastography imaging protocol can comprise additional acquisitions, which are not necessarily performed in synchrony with the rotational frequency signal. The at least temporary synchrony improves the image quality of the MR elastography imaging protocol.

Reference is made to the fact that the described methods and the described data processing unit as well as the described imaging device are merely preferred example embodiments of the invention and that the invention can be varied by a person skilled in the art, without departing from the scope of the invention provided it is specified by the claims.

BRIEF DESCRIPTION OF THE DRAWINGS/FIGURES

The invention will be illustrated below with reference to the accompanying figures using example embodiments. The illustration in the figures is schematic and highly simplified and not necessarily to scale.

Figure 2:
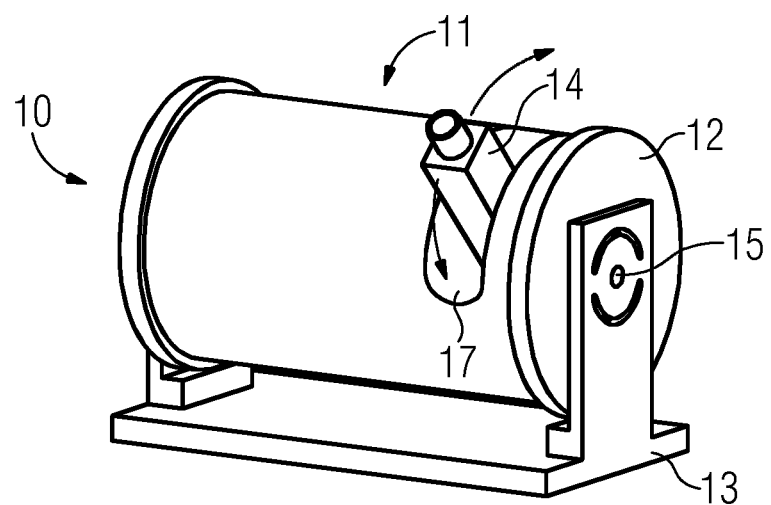
Figure 3:
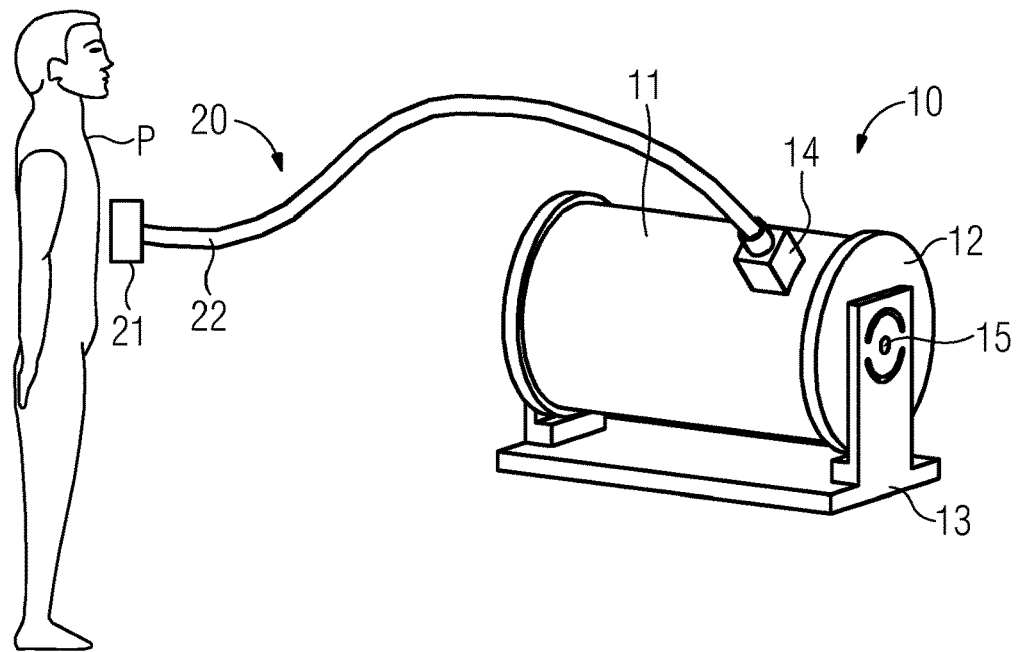
Figure 4:
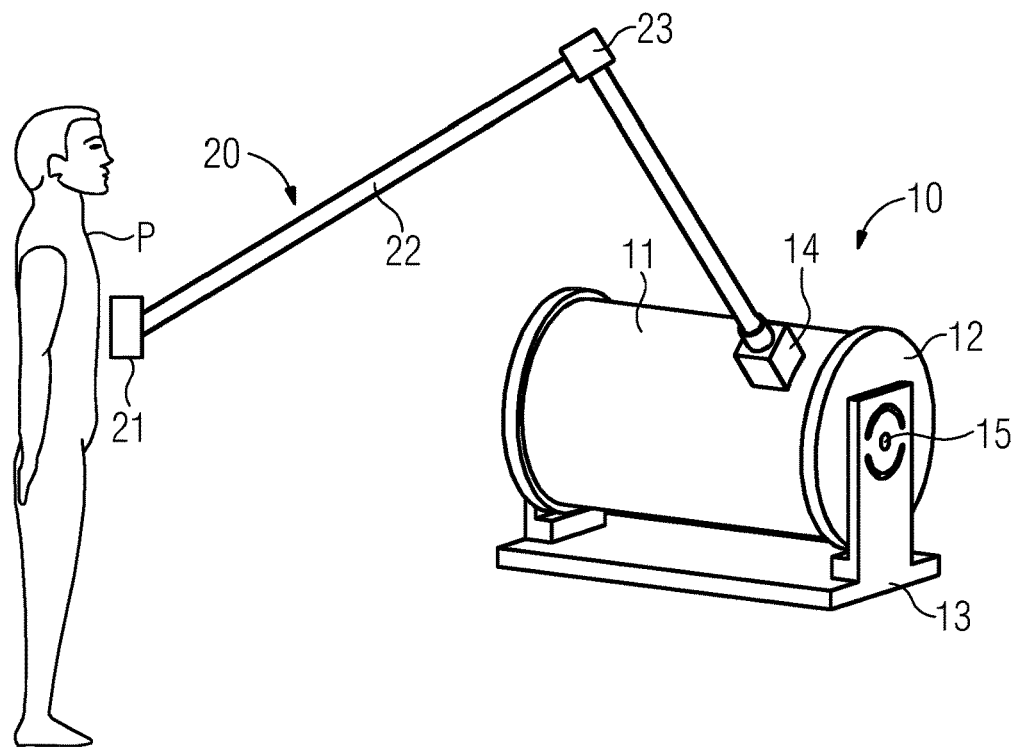
Figure 5:
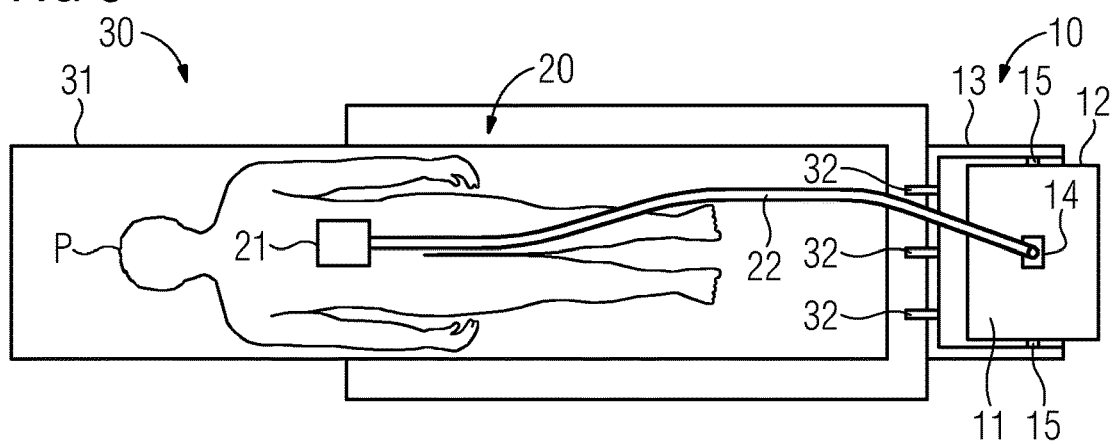
Figure 6:
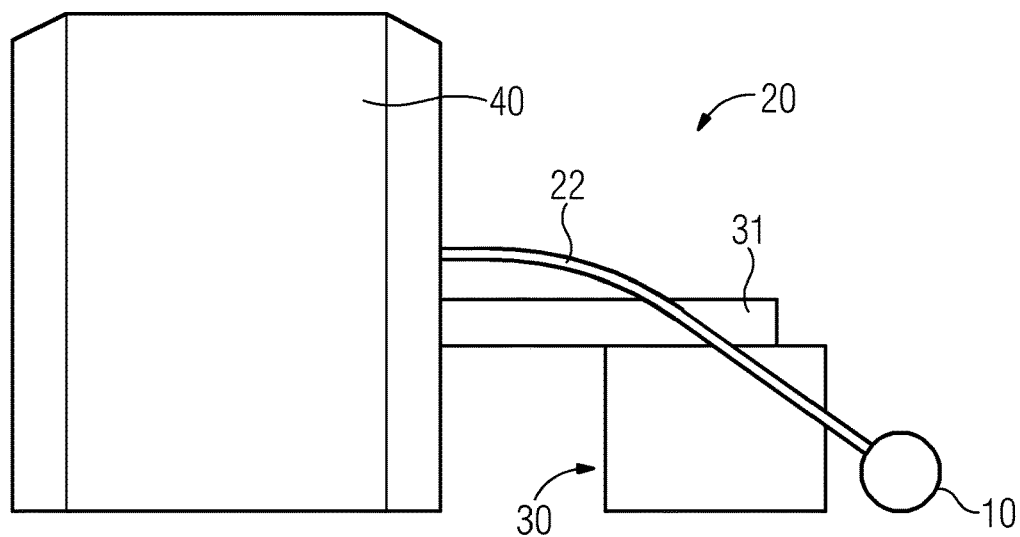
Figure 7:
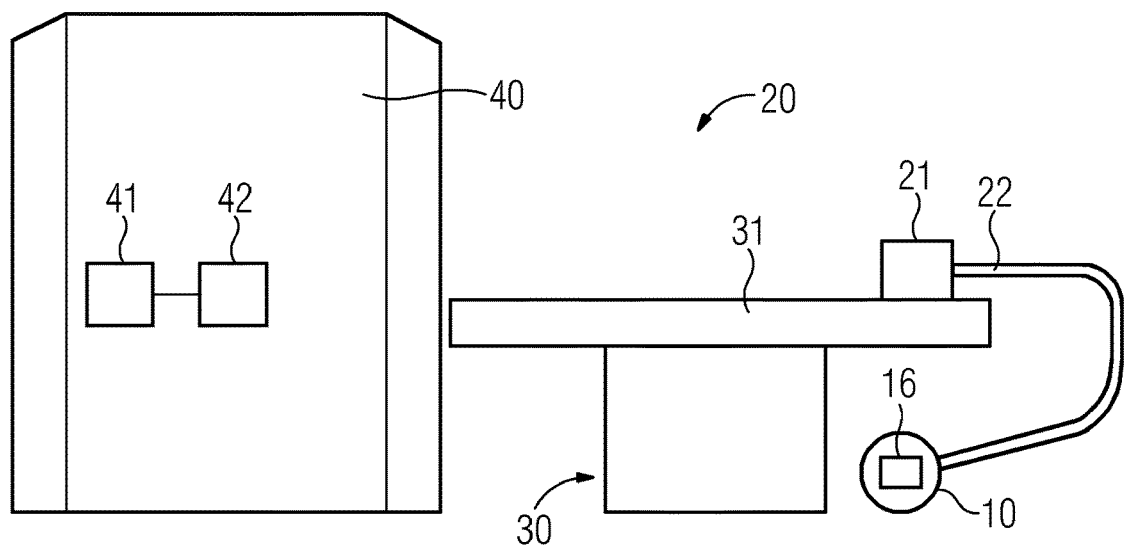

FIG. 1 shows a motor,
FIG. 2 shows a motor in an alternative embodiment,
FIG. 3 shows a MR elastography device,
FIG. 4 shows a MR elastography device in a further embodiment
FIG. 5 shows a patient table and
FIGS. 6 and 7 a MR tomography device in two different operating modes.

DETAILED DESCRIPTION

FIG. 1 shows a motor 10 in a perspective view. The motor 10 for a MR tomography room, wherein a MR tomography device for a MR elastography imaging protocol is arranged within the MR tomography room, comprises:
a rotational drive 11 for supplying rotational energy to power a MR elastography transducer 21, not shown in FIG. 1, usable during the MR elastography imaging protocol,
a container 12,
a support structure 13.

The rotational drive 11 is arranged within the container 12. The rotational drive 11 comprises in this embodiment a stepper motor to generate the rotational energy. The rotational drive 11 comprises a terminal 14 for connecting the MR elastography transducer 21 (not shown in FIG. 1) to the rotational drive 11. The terminal 14 is arranged in the wall of the container 12. In this embodiment, the container 12 is cylindric and the terminal 14 is arranged in the lateral wall.

The container 12 is fixed rigidly to the rotational drive 11 such that the trajectory of the terminal 14 substantially corresponds to a trajectory of the container 12. In this embodiment, the rotational drive 11 and the container 12 are movably mounted relative to the support structure 13.

The motor 10 further comprises a bearing means 15 configured such that the position of the terminal 14 relative to the support structure 13 is adaptable along a trajectory predetermined by the bearing means 15.

The rotational drive 11 is mounted to the support structure 13 via the bearing means 15. In this embodiment, the bearing means comprises a rotor bearing, wherein the support structure 13 is the stator and the rotational drive 11 is the rotor. The trajectory is highlighted by arrows and allows a radial rotation.

FIG. 2 shows the motor 10 in an alternative embodiment. In contrast to the embodiment shown in FIG. 1, the container 12 comprises a slit 17 and the terminal 14 is movably mounted relative to the slit 17. That is, the rotational drive 11 is movably mounted relative to the support structure 13 and the container 12.

FIG. 3 shows a MR elastography device 20 in a perspective view. The MR elastography device 20 comprises:
a motor 10, in particular the motor 10 shown in FIG. 1,
a MR elastography transducer 21 configured to transmit vibration to a patient P in dependence of the rotational energy during a MR elastography imaging protocol and
a driveshaft 22 which is connected to the terminal 14 of the motor 10 to confer the rotational energy from the rotational drive 11 to the MR elastography transducer 21.

In this embodiment, the terminal 14 is configured to provide a locknut connection for this connection.

FIG. 4 shows a further embodiment of the MR elastography device 20 in a perspective view. In addition to the embodiment shown in FIG. 3 the driveshaft 22 comprises a universal joint 23.

FIG. 5 shows in a top view the MR elastography device 20 of FIG. 3 being integrated into a patient table 30. The patient table 30 is configured to be operated within a MR room and comprises
a tabletop 31 for bearing a patient P,
a holding means 32,
the motor 10,
wherein the support structure 13 of the motor 10 is fastened to the patient table 30 via the holding means 32 and
wherein the tabletop 31 is movable relative to the holding means 32.

In this embodiment, the holding means 32 and the support structure 13 comprise such a configuration that a longitudinal axis of the tabletop 31 is parallel to at least one spatial axis of the trajectory. Furthermore, the configuration is embodied such that the trajectory separates the tabletop 31 in two equally sized areas. The terminal 14 is located in the middle between the bearing means 15 and in the middle relative to the short axis of the tabletop 31. Additionally, a damping means can be provided between the support structure 13 and the patient table 30 to reduce mechanical vibrations.

FIGS. 6 and 7 show a MR tomography device 40 in two different operating modes. The first operating mode is shown in FIG. 6, when the patient table 30 is in the bore, and the second operating mode is shown in FIG. 7, when the patient table 30 is outside the bore.

The MR tomography device 40 for a MR elastography imaging protocol comprises:
a main magnet for generating a main magnetic field and
a MR elastography device 20.

In these two embodiments of FIGS. 6 and 7, the driveshaft 22 is configured to bend in a loop depending on the position of the MR elastography transducer 21 relative to the terminal 14. In FIG. 6 the MR elastography transducer 21 is relatively far from the terminal 14 compared to the position in FIG. 7. Furthermore, the driveshaft 22 is made from a flexible plastic material, such as PEEK. Additionally, it is shown, that a rotational axis of the container 12 is parallel to the floor, on which the patient table 30 is arranged.

FIG. 7 shows a preferred modification of the MR tomography device 40 shown in FIG. 6 in addition to the different patient table's 30 position.

The motor 10 comprises an output interface 16 which is configured to provide a rotational frequency signal relative to a rotational frequency and/or phase of the rotational drive. The MR tomography device 40 comprises an input interface 41 which is configured to receive a rotational frequency signal relative to a rotational frequency and/or phase of the rotational drive and a control unit 42 configured to control the imaging of the patient P according to the MR elastography imaging protocol such that the imaging is performable at least temporarily in synchrony with the rotational frequency signal. The input interface 41 is configured to receive the rotational frequency signal from the output interface 16, e.g. by a wired or wireless connection.

What is claimed is:

1. A motor for a magnetic resonance tomography room, wherein a magnetic resonance (MR) tomography device for a MR elastography imaging protocol is arranged within the MR tomography room, the motor comprising:
   a rotational drive for supplying rotational energy to power a MR elastography transducer usable during the MR elastography imaging protocol;
   a support structure; and
   a container,
   wherein the rotational drive comprises a terminal for connecting the MR elastography transducer to the rotational drive,
   wherein a bearing means is configured such that a position of the terminal relative to the support structure is adaptable along a trajectory predetermined by the bearing means,
   wherein the rotational drive is mounted to the support structure via the bearing means, and
   wherein the rotational drive is arranged within the container.

2. The motor as claimed in claim 1,
   wherein the bearing means comprises a rotor bearing, and
   wherein the support structure is a stator and the rotational drive is a rotor.

3. The motor as claimed in claim 1,
   wherein the container is fixed rigidly to the rotational drive such that the trajectory of the terminal substantially corresponds to a trajectory of the container, and
   wherein the terminal is arranged in a lateral wall of the container.

4. The motor as claimed in claim 1,
   wherein the container comprises a slit, and
   wherein the terminal is movably mounted relative to the slit.

5. The motor as claimed in claim 1, wherein the motor comprises an output interface configured to provide a rotational frequency signal relative to a rotational frequency and/or phase of the rotational drive.

6. A patient table for a magnetic resonance (MR) room, comprising:
   a tabletop for bearing a patient;
   a holding means; and
   a motor comprising:
      a rotational drive for supplying rotational energy to power a MR elastography transducer usable during a MR elastography imaging protocol; and
      a support structure,
   wherein the rotational drive comprises a terminal for connecting the MR elastography transducer to the rotational drive,
   wherein a bearing means is configured such that a position of the terminal relative to the support structure is adaptable along a trajectory predetermined by the bearing means,
   wherein the rotational drive is mounted to the support structure via the bearing means,
   wherein the support structure of the motor is fastened to the patient table via the holding means, and
   wherein the tabletop is movable relative to the holding means.

7. The patient table as claimed in claim 6,
   wherein the holding means and the support structure comprise a configuration such that a longitudinal axis of the tabletop is parallel to at least one spatial axis of the trajectory.

8. The patient table as claimed in claim 7,
   wherein the configuration is embodied such that the trajectory separates the tabletop into two equally-sized areas.

9. The patient table as claimed in claim 6,
   wherein a damping means is provided between the support structure and the patient table to reduce mechanical vibrations.

10. A magnetic resonance (MR) elastography device, comprising:
    a MR elastography transducer configured to transmit vibration to a patient in dependence of rotational energy during a MR elastography imaging protocol;
    a motor comprising:
       a rotational drive for supplying the rotational energy to power the MR elastography transducer usable during the MR elastography imaging protocol; and
       a support structure,
    wherein the rotational drive comprises a terminal for connecting the MR elastography transducer to the rotational drive;
    a driveshaft connected to the terminal of the motor and configured to confer the rotational energy from the rotational drive to the MR elastography transducer; and
    wherein a bearing means is configured such that a position of the terminal relative to the support structure is adaptable along a trajectory predetermined by the bearing means,
    wherein the rotational drive is mounted to the support structure via the bearing means, and
    wherein the driveshaft is configured to bend in a loop depending on the position of the MR elastography transducer relative to the terminal.

11. The MR elastography device as claimed in claim 10, further comprising:
    a patient table,
    wherein the support structure of the motor is fastened to the patient table via a holding means.

12. The MR elastography device as claimed in claim 11, wherein the patient table comprises:
    a tabletop for bearing a patient, and
    wherein the tabletop is movable relative to the holding means.

13. The MR elastography device as claimed in claim 10, wherein the driveshaft comprises a universal joint.

14. A magnetic resonance (MR) tomography device for a MR elastography imaging protocol, comprising:
    a main magnet for generating a main magnetic field;
    a MR elastography device comprising:
       a motor comprising:
          a rotational drive for supplying rotational energy to power a MR elastography transducer usable during the MR elastography imaging protocol; and
          a support structure,
       wherein the rotational drive comprises a terminal for connecting the MR elastography transducer to the rotational drive,
       wherein a bearing means is configured such that a position of the terminal relative to the support structure is adaptable along a trajectory predetermined by the bearing means, and
       wherein the rotational drive is mounted to the support structure via the bearing means;
    a MR elastography transducer configured to transmit vibration to a patient in dependence of the rotational energy during a MR elastography imaging protocol; and a driveshaft connected to the terminal of the motor to confer the rotational energy from the rotational drive to the MR elastography transducer;

an input interface configured to receive a rotational frequency signal relative to a rotational frequency and/or phase of the rotational drive; and a control unit configured to control an imaging of the patient according to the MR elastography imaging protocol such that the imaging is performable at least temporarily in synchrony with the rotational frequency signal.

15. The MR tomography device as claimed in claim 14, further comprising:

a patient table, wherein the support structure of the motor is fastened to the patient table via a holding means.

16. The MR tomography device as claimed in claim 15, wherein the patient table comprises:

a tabletop for bearing a patient, and wherein the tabletop is movable relative to the holding means.

17. A motor for a magnetic resonance tomography room, wherein a magnetic resonance (MR) tomography device for a MR elastography imaging protocol is arranged within the MR tomography room, the motor comprising:

a rotational drive for supplying rotational energy to power a MR elastography transducer usable during the MR elastography imaging protocol; and a support structure, wherein the rotational drive comprises a terminal for connecting the MR elastography transducer to the rotational drive, wherein a bearing means is configured such that a position of the terminal relative to the support structure is adaptable along a trajectory predetermined by the bearing means, wherein the rotational drive is mounted to the support structure via the bearing means, and wherein the motor comprises an output interface configured to provide a rotational frequency signal relative to a rotational frequency and/or phase of the rotational drive.

18. A magnetic resonance (MR) elastography device, comprising:

a MR elastography transducer configured to transmit vibration to a patient in dependence of rotational energy during a MR elastography imaging protocol;

a motor comprising:

a rotational drive for supplying the rotational energy to power the MR elastography transducer usable during the MR elastography imaging protocol; and a support structure, wherein the rotational drive comprises a terminal for connecting the MR elastography transducer to the rotational drive; and a driveshaft connected to the terminal of the motor and configured to confer the rotational energy from the rotational drive to the MR elastography transducer, wherein a bearing means is configured such that a position of the terminal relative to the support structure is adaptable along a trajectory predetermined by the bearing means, wherein the rotational drive is mounted to the support structure via the bearing means, and wherein the driveshaft comprises a universal joint.

* * * * *